(12) United States Patent
Erman et al.

(10) Patent No.: US 7,652,067 B2
(45) Date of Patent: Jan. 26, 2010

(54) AQUEOUS COMPOSITIONS CONTAINING MONOESTER SALTS

(75) Inventors: Mark B. Erman, Atlantic Beach, FL (US); Joe W. Snow, Kingsland, GA (US)

(73) Assignee: Millenium Specialty Chemicals, Inc., Houston, TX (US)

( * ) Notice: Subject to any disclaimer, the term of this patent is extended or adjusted under 35 U.S.C. 154(b) by 512 days.

(21) Appl. No.: 11/517,798

(22) Filed: Sep. 8, 2006

(65) Prior Publication Data

US 2008/0085933 A1 Apr. 10, 2008

(51) Int. Cl.
*A61K 31/225* (2006.01)
(52) U.S. Cl. .................................................... 514/548
(58) Field of Classification Search .................. 514/548
See application file for complete search history.

(56) References Cited

U.S. PATENT DOCUMENTS

| | | | |
|---|---|---|---|
| 3,703,481 A | 11/1972 | Barker et al. | |
| 3,762,932 A | 10/1973 | Buddemeyer et al. | 99/92 |
| 4,299,737 A | 11/1981 | Meffert et al. | 252/522 R |
| 4,596,795 A | 6/1986 | Pitha | 514/58 |
| 4,714,565 A | 12/1987 | Wevers et al. | 252/174.19 |
| 5,081,104 A | 1/1992 | Orson, Sr. | 512/3 |
| 5,320,863 A | 6/1994 | Chung et al. | 426/650 |
| 5,374,614 A | 12/1994 | Behan et al. | 512/3 |
| 5,635,190 A | 6/1997 | Cheetham et al. | 424/401 |
| 5,725,865 A | 3/1998 | Mane et al. | 424/401 |
| 5,843,466 A * | 12/1998 | Mane et al. | 424/401 |
| 6,121,315 A | 9/2000 | Nair et al. | 514/494 |
| 6,365,215 B1 | 4/2002 | Grainger et al. | 426/535 |
| 2006/0084589 A1 | 4/2006 | Vlad et al. | 510/417 |

FOREIGN PATENT DOCUMENTS

| | | |
|---|---|---|
| EP | 0 282 289 | 9/1988 |
| EP | 1493336 A2 | 1/2005 |
| WO | WO 97/07771 | 3/1997 |
| WO | WO 98/11867 | 3/1998 |
| WO | WO 2007/100450 | 9/2007 |

OTHER PUBLICATIONS

Hawley's Condensed Chemical Dictionary definition of hydrotrope, 1997, revised by Richard J. Lewis and published by Van Nostrand Reinhold p. 594.*
Bansho K. et al., "Mono-alcohol ester of maleic acid prodn.—by reacting maleic anhydride and alcohol in presence of alkali metal salt of organic acid under nitrogen atmos" WPI/ Thomson, Feb. 24, 1979, XP002444425 abstract.
Shimizu T. et al., "Synthesis of Dicarboxylic Monoesters With Cyclic Anhydrides Under High Pressure" Synlett, Thieme International, Stuttgart, DE, No. 6, Jun. 1995, pp. 650-652.

* cited by examiner

*Primary Examiner*—David J Blanchard
*Assistant Examiner*—Kortney L Klinkel
(74) *Attorney, Agent, or Firm*—Jonathan L. Schuchardt

(57) ABSTRACT

Clear aqueous compositions comprising water, a hydrophobic organic compound, and from about 2 to about 50 wt. % of a solubilizer are disclosed. The solubilizer is an alkali metal or alkaline earth metal salt of a monoester of a saturated $C_6$-$C_{20}$ alcohol and a saturated dicarboxylic acid. The monoester salts are remarkably effective for solubilizing a wide variety of hydrophobic organic compounds in water to provide aqueous compositions that have excellent stability and outstanding clarity. The compositions are valuable for the cosmetic, agrochemical, coatings, pharmaceutical, and flavor & fragrance industries.

9 Claims, No Drawings

AQUEOUS COMPOSITIONS CONTAINING MONOESTER SALTS

FIELD OF THE INVENTION

The invention relates to clear aqueous compositions that contain a solubilized hydrophobic organic compound. The compositions are valuable for formulating flavors, physiological cooling or warming agents, agrochemicals, fragrances, cosmetics, and pharmaceuticals.

BACKGROUND OF THE INVENTION

It is often desirable to make clear aqueous compositions that incorporate organic components that are either insoluble or only slightly soluble in water. The problem is ubiquitous in formulating, for example, certain pharmaceutical or flavor & fragrance applications. Some related art teachings refer to such aqueous compositions as solutions, while others describe them as transparent oil-in-water microemulsions. Either way, the goal is essentially the same: to solubilize organic compounds in water to obtain a clear mixture.

Many solubilizers have been identified. In one well-known approach, a water-miscible co-solvent (ethanol, acetone, propylene glycol, dimethylsulfoxide, glycol ethers, or the like) is simply added. For one example, see U.S. Pat. No. 5,081,104. Unfortunately, even traces of co-solvents in the final product are often unacceptable.

Inclusion complexes with cyclodextrins (see, e.g., U.S. Pat. No. 4,596,795) are another way to solubilize hydrophobic components. However, these require tedious research to identify cyclodextrins that are just the right size to accept the hydrophobic substrates, and they also require that the inclusion complex be water soluble. Moreover, because of its high molecular weight, a large proportion of cyclodextrin is normally needed.

Other solubilizers for making clear aqueous compositions that contain a hydrophobic component include: surfactants or mixtures of surfactants (see, e.g., U.S. Pat. No. 5,374,614 or 5,320,863); epoxide-glycol reaction products (U.S. Pat. No. 4,299,737); ester reaction products of a $C_1$-$C_4$ alcohol and a $C_8$-$C_{16}$ alkylene-substituted succinic acid derivative (German Pat. DE 2 915 948); monoalkyl citrates (U.S. Pat. No. 5,635,190); and combinations of a surfactant and a solubilizer, which may be a $C_2$-$C_7$ dicarboxylic acid or a salt thereof (U.S. Pat. Appl. Pub. No. 2006/0084589). None of these references discloses clear aqueous compositions that contain a monoester salt of the type described and claimed herein.

Salts of monoesters derived from a saturated $C_6$-$C_{20}$ alcohol and a saturated dicarboxylic acid (e.g., glutaric acid, succinic acid, adipic acid) are generally known. They have been taught for use in making bakery products (U.S. Pat. No. 3,762,932), bar soaps (Canadian Pat. No. 1,329,104), and concentrated liquid laundry detergents containing less than 50 wt. % water (U.S. Pat. No. 4,714,565). In the flavor & fragrance industry, such salts have been recognized as physiological coolants that can be used at part-per-million levels in such aqueous compositions as mouthwashes and beverages (see U.S. Pat. Nos. 5,725,865; 6,121,315; and 6,365,215). None of the references teaches to use at least 2 wt. % of the monoester salt to solubilize a hydrophobic organic compound in an aqueous composition that contains at least 55 wt. % water.

In sum, numerous industries would benefit from the availability of more ways to solubilize hydrophobic organic compounds in water to provide clear aqueous compositions. In particular, the pharmaceutical and flavor & fragrance industries are always looking for better ways to solubilize vitamins, physiological cooling or warming agents, medicines, dietary supplements, cosmetics, flavors, fragrances, or combinations of these, in aqueous media. Preferred compositions would avoid co-solvents or cyclodextrins. Ideally, the compositions would be clear, stable, economical, and easy to formulate.

SUMMARY OF THE INVENTION

In one aspect, the invention is a clear aqueous composition. The composition comprises water, a hydrophobic organic compound, and a solubilizer. In particular, the composition comprises from about 55 to about 98 wt. % of water, from about 0.1 to about 10 wt. % of the hydrophobic organic compound, and from about 2 to about 50 wt. % of a solubilizer. The solubilizer is an alkali metal or alkaline earth metal salt of a monoester of a saturated $C_6$-$C_{20}$ alcohol and a saturated dicarboxylic acid. The invention includes processes for making the clear aqueous compositions.

We surprisingly found that the monoester salts described herein are remarkably effective for solubilizing a wide variety of hydrophobic organic compounds in water. When used at 2 to 50 wt. %, the monoester salts provide aqueous compositions that have excellent stability and outstanding clarity. The compositions have value for a wide range of industrial applications, particularly in the cosmetic, agrochemical, coatings, pharmaceutical, and flavor & fragrance industries.

DETAILED DESCRIPTION OF THE INVENTION

Aqueous compositions of the invention comprise mostly water. In particular, the compositions comprise from about 55 to about 98 wt. %, more preferably from about 60 to about 90 wt. %, and most preferably from about 65 to about 85 wt. % of water.

The clear aqueous compositions include a hydrophobic organic compound. By "hydrophobic organic compound," we mean one that is insoluble or is at most only slightly soluble in water. Preferably, the solubility is less than 1 wt. %, more preferably less than 0.1 wt. %. The hydrophobic organic compound will have at least five carbon atoms and can have one or more of a variety of different functionalities. It can be aromatic or aliphatic, linear, branched or cyclic, and saturated or unsaturated. Thus, the hydrophobic organic compound can be a hydrocarbon, alkyl or aryl halide, alcohol, phenol, ether, ester, ketone, aldehyde, nitrile, amine, amide, nitro compound, heterocycle, or the like, provided it is at most only sparingly soluble in water.

Particularly preferred hydrophobic organic compounds are useful in the agrochemical, pharmaceutical, essential oils, coatings, healthcare, cosmetic, dietary supplement, or flavor & fragrance industries. Others are biologically active. The compositions comprise from about 0.1 to about 10 wt. % of the hydrophobic organic compound. More preferred compositions comprise from about 0.2 to about 5 wt. % of the hydrophobic organic compound.

Hydrophobic organic compounds useful in the flavor & fragrance industry include perfumes, flavoring agents, and physiological cooling or warming agents. Just a few examples: d-limonene, p-cymene, citronellol, l-menthol, citronellyl nitrile, l-carvone, l-menthyl lactate, N-ethyl-p-menthane-3-carboxamide (WS-3), N,2,3-trimethyl-2-(1-methylethyl)-butanamide (WS-23), N-ethoxycarbonylmethyl-p-menthane-3-carboxamide (WS-5), menthone glyceryl ketal, 3-l-menthoxy-1,2-propanediol (TK-10), monomenthyl glutarate (MMG), monomenthyl succinate (MMS), isopulegol, menthol, menthone, p-menthane-3,8-diol, vanillyl butyl ether (VBE), capsaicin, vitamin E, linalool, linalyl acetate, and the like. Mixtures of hydrophobic organic compounds can be used (see, e.g., Example 10 below).

Importantly, the clear aqueous compositions include a monoester salt solubilizer. Suitable solubilizers are alkali metal or alkaline earth metal salts of monoesters of a saturated $C_6$-$C_{20}$ alcohol and a saturated dicarboxylic acid. Most conveniently, the monoesters are neutralized reaction products of cyclic anhydrides and $C_6$-$C_{20}$ alcohols, although they can be made other ways.

Preferably, the monoester salt derives from a readily available saturated, cyclic anhydride such as glutaric anhydride, 2-methylglutaric anhydride, 3-methylglutaric anhydride, 2-methylsuccinic anhydride, succinic anhydride, or adipic anhydride. Glutaric, succinic, and adipic anhydrides are particularly preferred.

The monoester salt derives from a saturated, $C_6$-$C_{20}$ alcohol. The alcohol can be linear, branched, or cyclic. Examples include 1-hexanol, 1-octanol, 1-decanol, 2-ethyl-1-hexanol, cyclohexanol, 4-methylcyclo-hexanol, l-menthol, 1-decanol, 1-dodecanol, and the like, and mixtures thereof. 1-Octanol and l-menthol are particularly preferred.

The monoester salts incorporate an alkali or alkaline earth metal cation, such as sodium, lithium, potassium, cesium, magnesium, calcium, or barium. Preferably, the metal ion is sodium, potassium, lithium, or magnesium.

Preferred monoester salts have the general formula $M^{n+}$ [A–]$_n$ wherein M is an alkali metal or alkaline earth metal, n is 1 or 2, m is an integer from 1 to 3, and A– has the structure:

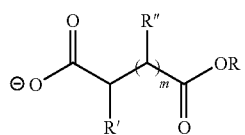

in which R is a linear, branched, or cyclic $C_6$-$C_{20}$ alkyl group, and each R' or R" is independently hydrogen, $C_1$-$C_8$ alkyl, or $C_6$-$C_8$ aryl. More preferably, M is sodium or potassium, m is 2, R is n-octyl or l-menthyl, and each of R' and R" is hydrogen.

Particularly preferred monoester salts are alkali metal glutarates, succinates, or adipates derived from 1-menthol or 1-octanol. Examples include alkali metal salts of monooctyl glutarate, monomenthyl glutarate, monomenthyl 3-methylglutarate, monomenthyl 2-methylglutarate, monomenthyl succinate, monomenthyl 2-methylsuccinate, monomenthyl adipate, and mixtures thereof.

The clear aqueous compositions comprise from about 2 to about 50 wt. %, preferably from about 4 to about 30 wt. %, and most preferably from about 5 to about 20 wt. % of the monoester salt. Often, the monoester salt does more than just solubilize the hydrophobic organic compound in water. Preferably, the monoester salt provides physiological cooling, physiological warming, flavor or fragrance enhancement, or other benefits. Such is the case with the glutarate and succinate salts noted above, which are well-known physiological coolants (see U.S. Pat. Nos. 5,725,865 and 6,365,215).

While these monoester salts have been described previously, their potential benefit as solubilizers for clear aqueous compositions was unappreciated. We surprisingly found that the monoester salts, when used at 2 to 50 wt. %, provide aqueous compositions of hydrophobic compounds that have exceptional clarity and excellent stability (see Examples 1-16, below).

The aqueous compositions are easy to make. In one convenient approach, the monoester salt is generated in the presence of the hydrophobic organic compound (see Examples 1 and 12). In a typical example, a solution of aqueous base (sodium hydroxide, potassium hydroxide, sodium carbonate, potassium carbonate, sodium bicarbonate, potassium bicarbonate, or the like) is added to a mixture that contains the hydrophobic organic compound and a monoester derived from a saturated $C_6$-$C_{20}$ alcohol and a saturated dicarboxylic acid. In other words, the aqueous base is combined with a mixture comprising the hydrophobic organic compound and the acid form of the monoester salt. Addition of the base solution generates the monoester salt in situ and produces a clear aqueous solution of the hydrophobic organic compound. When a carbonate or bicarbonate is the base, carbon dioxide evolves as the base is added and for a while thereafter.

In another convenient method, the monoester salt is formed before the hydrophobic organic compound is introduced. Example 5 (below) illustrates this approach. Thus, combining a monoester derived from a saturated $C_6$-$C_{20}$ alcohol and a saturated dicarboxylic acid with aqueous base provides a solution of the monoester salt. Combination of the hydrophobic organic compound with this solution gives a clear aqueous solution of the hydrophobic organic compound.

In a preferred process, l-menthol reacts with a saturated cyclic anhydride to produce a mixture comprising crude monoester. The crude monoester is washed with water to remove unreacted anhydride and dicarboxylic acid. Finally, the monoester is reacted with a base to produce a clear aqueous solution comprising l-menthol and a monoester salt. In a preferred embodiment, the cyclic anhydride is glutaric anhydride and the monoester is monomenthyl glutarate (see Example 12). The aqueous composition will be particularly useful for formulating physiological coolants.

It may be desirable to dilute the aqueous compositions with water. The amount of water that can be added while maintaining a clear aqueous solution depends on many factors known to those skilled in the art, including the nature of the hydrophobic organic compound, the particular monoester salt, the concentration of each of these components, and other factors. In general, the desirability of diluting the aqueous composition is determined empirically. Occasionally, too much water provides an emulsion, which may or may not be a desirable outcome depending upon the intended use. Thus, the invention includes emulsions made by diluting the clear aqueous compositions with enough water to form an emulsion. Many of the examples below (see, for instance, Examples 4, 7, 8, 11, and 12) show that dilution can be used to provide less-concentrated yet clear aqueous solutions of the invention. Other examples (see Examples 1, 3, and 6) show how to make emulsions from the clear aqueous solutions.

The invention includes consumer products that are prepared from or which comprise the clear aqueous compositions. In particular, the consumer product may be a flavor blend, food, confectionary, beverage, chewing gum, dental floss, toothpaste, mouthwash, anti-plaque composition, anti-gingivitis composition, throat lozenge, throat drop, antacid tablet, pharmaceutical composition, medicinal composition, or the like. The clear aqueous compositions might also be used in the manufacture of skin or scalp-treatment products such as a cosmetic, shampoo, lotion, deodorant, aftershave, shaving gel, shaving cream, fragrance, soap, or the like.

The following examples merely illustrate the invention. Those skilled in the art will recognize many variations that are within the spirit of the invention and scope of the claims.

Example 1

Aqueous Dodecane Composition

Aqueous sodium bicarbonate (98 g, 8.8% solution) is added over about 20 minutes to a stirred mixture of monomenthyl glutarate ("MMG," 25 g) and dodecane (3.0 g). After the addition is complete and $CO_2$ evolution stops, the mixture is stirred for 2 h and is then allowed to settle. The resulting mixture is a clear, homogeneous solution of dodecane (~2.5%) in aqueous sodium monomenthyl glutarate (Na-MMG).

In a control experiment, stirring dodecane (12 g) with water (876 g) for 2 h fails to produce a homogeneous mixture. After settling, the layers are separated to give about 876 g of water and 11.6 g of undissolved dodecane.

The example shows that dodecane dissolves in aqueous Na-MMG at least about 50 times better than it does in pure water.

Dilution of a portion of the clear aqueous composition with an equal volume of water produces a clear solution that emulsifies within two days.

Example 2

Aqueous d-Limonene Composition

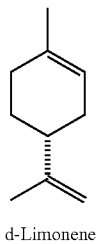

d-Limonene

The procedure of Example 1 is followed using d-limonene (4.5 g) instead of dodecane. The resulting mixture is a clear, homogeneous solution of d-limonene (~3.6%) in aqueous Na-MMG.

In a control experiment similar to that of Example 1, 18 g of d-limonene in water fails to produce a homogeneous mixture. After settling, the layers are separated to give about 876 g of water and 17.5 g of undissolved d-limonene.

The example shows that d-limonene dissolves in aqueous Na-MMG at least about 60 times better than it does in pure water.

Example 3

Aqueous p-Cymene Composition

The procedure of Example 1 is followed using p-cymene (4.5 g). The resulting mixture is a clear, homogeneous solution of p-cymene (~3.6%) in aqueous Na-MMG. In a control experiment, p-cymene and water fail to produce a homogeneous mixture.

Dilution of a portion of the clear aqueous composition with an equal volume of water produces a solution that emulsifies within 2 days.

Example 4

Aqueous Citronellol Composition

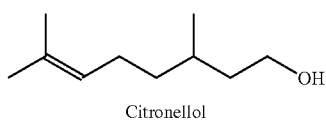

Citronellol

The procedure of Example 1 is followed using citronellol (4.5 g). The resulting mixture is a clear, homogeneous solution of citronellol (~3.6%) in aqueous Na-MMG. Dilution with an equal volume of water produces a solution that remains clear for more than 40 days. In a control experiment, citronellol and water fail to produce a homogeneous mixture.

Example 5

Aqueous l-Menthol Composition

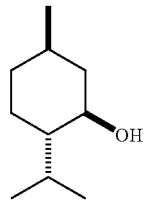

l-Menthol

A clear aqueous solution of Na-MMG is obtained by reacting monomenthyl glutarate (25 g) with aqueous sodium bicarbonate (98 g of 8.8% solution). Crystalline l-menthol (3 g) is added, and the mixture is warmed to about 47° C. to melt the menthol. The mixture stirs for about 2 h and is allowed to cool to ambient temperature. The resulting mixture is a clear, homogeneous solution of l-menthol (~2.5%) in aqueous Na-MMG. An organoleptic test shows that this solution has a strong physiological cooling effect. Dilution with an equal volume of water produces a solution that remains clear for more than 40 days.

In a control experiment, l-menthol (12 g) is stirred with water (876 g) for 2 h, initially at 47° C., then at ambient temperature, but no homogeneous mixture results. Menthol is isolated by filtration. Gas chromatography analysis shows that the clear aqueous solution contains 0.06% menthol.

The example shows that l-menthol dissolves in aqueous Na-MMG at least about 40 times better than it does in pure water.

Example 6

Aqueous Citronellyl Nitrile Composition

The procedure of Example 1 is followed using citronellyl nitrile (4.5 g). The resulting mixture is a clear, homogeneous solution of citronellyl nitrile (~3.6%) in aqueous Na-MMG. In a control experiment, citronellyl nitrile and water fail to produce a homogeneous mixture.

Dilution of the clear aqueous composition with an equal volume of water immediately produces an emulsion.

Example 7

Aqueous l-Carvone Composition

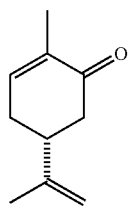

l-Carvone

The procedure of Example 1 is followed using l-carvone (4.5 g). The resulting mixture is a clear, homogeneous solution of l-carvone (~3.6%) in aqueous Na-MMG. Dilution with an equal volume of water produces a solution that remains clear for more than 40 days. In a control experiment, l-carvone and water fail to produce a homogeneous mixture.

Example 8

Aqueous l-Menthyl Lactate Composition

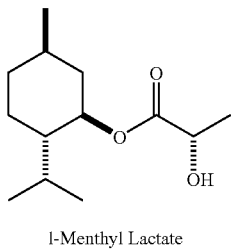

l-Menthyl Lactate

The procedure of Example 1 is followed using l-menthyl lactate (1.5 g). The resulting mixture is a clear homogeneous solution of l-menthyl lactate (~1.25%) in aqueous Na-MMG. Dilution with an equal volume of water produces a solution that remains clear for more than 40 days. In a control experiment, l-menthyl lactate and water fail to produce a homogeneous mixture.

Example 9

Aqueous N-Ethyl-p-menthane-3-carboxamide Composition

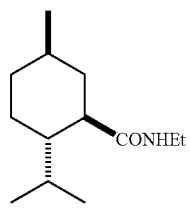

N-Ethyl-p-menthane-3-carboxamide (WS-3)

Aqueous sodium bicarbonate (196 g, 8.8% solution) is added to a stirred mixture of monomenthyl glutarate (50 g) and N-ethyl-p-menthane-3-carboxamide ("WS-3," 2.0 g). After the addition is complete and $CO_2$ evolution stops, the mixture is stirred for 1 h and is then allowed to sit overnight. The resulting mixture is a clear, homogeneous solution of WS-3 (~0.83%) in aqueous Na-MMG. The mixture (pH 7.4) exhibits a strong cooling effect when tested organoleptically.

More WS-3 (1.0 g) is added to the aqueous composition. The mixture stirs for 1 h and is allowed to stand overnight. The mixture is filtered to remove undissolved crystals (0.6 g). The filtrate (~1.0% of WS-3) exhibits a strong cooling effect when tested organoleptically. In a separate experiment, the solubility of WS-3 in pure water at 20° C. is found to be ~0.03%. The example shows that solubility of WS-3 in aqueous Na-MMG is about 33 times better than it is in pure water.

Example 10

Aqueous Coolant Cocktail Composition

Commercially available WinSense™ 500 coolant mixture (product of Millennium Specialty Chemicals) contains N,2,3-trimethyl-2-(1-methylethyl)butanamide (WS-23), N-ethyl-p-menthane-3-carboxamide (WS-3) and l-menthyl Lactate in the amounts shown below.

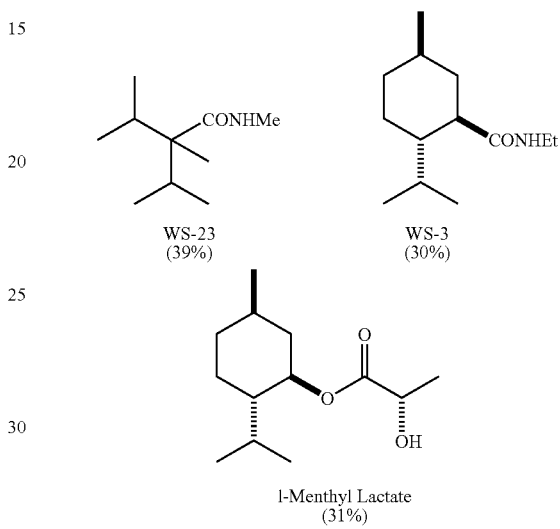

Physiological Cooling Cocktail WinSense 500

The procedure of Example 1 is followed using WinSense 500 coolant mixture (3.0 g). The resulting mixture is a clear, homogeneous solution of WinSense 500 (~1.25%) in aqueous Na-MMG. Dilution with an equal volume of water produces a solution that remains clear for more than 40 days. In a control experiment, WinSense 500 and water fail to produce a homogeneous mixture.

Example 11

Aqueous Vitamin E (α-Tocopherol) Composition

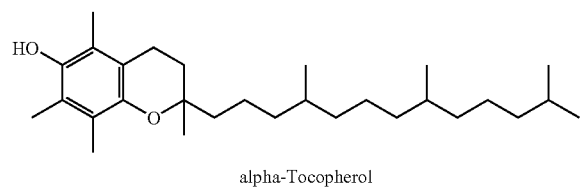

alpha-Tocopherol

The procedure of Example 1 is followed using α-tocopherol (1.5 g). The resulting mixture is a clear, homogeneous solution of α-tocopherol (~1.25%) in aqueous Na-MMG. Dilution with an equal volume of water produces a solution that remains clear for more than 40 days. In a control experiment, α-tocopherol and water fail to produce a homogeneous mixture.

Example 12

Aqueous Composition of Na-MMG, l-Menthol, and DMG

A mixture of l-menthol (200 g), glutaric anhydride (146 g), and sodium carbonate (3.8 g) stirs for 5 h at 90° C. to give a mixture containing l-menthol, MMG, dimethyl glutarate (DMG), and traces of glutaric acid and glutaric anhydride. The mixture is washed overnight with water (700 g) at ambient temperature to remove glutaric acid and glutaric anhydride. After washing, the mixture contains (by GC): l-menthol (16%), MMG (77%), and dimethyl glutarate (7%). The organic layer is separated and filtered through sodium sulfate. The product stirs for 1 h with aqueous $NaHCO_3$ (1370 g of 8.8% solution) and is then diluted with water (700 g) to give a clear homogeneous solution containing l-menthol (1.2%), Na-MMG (12.7%), and DMG (0.6%). Dilution with an equal volume of water produces a solution that remains clear for more than 40 days.

Example 13

Aqueous p-Cymene Composition

The procedure of Example 1 is followed except that monooctyl glutarate (MOG, 22.6 g) and p-cymene (5 g) are used. The resulting mixture is a clear, homogeneous solution of p-cymene (~4.4%) in aqueous sodium monooctyl glutarate (Na-MOG).

Example 14

Aqueous Linalool Composition

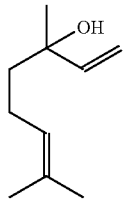

Linalool

The procedure of Example 1 is followed except that MOG (22.6 g) and linalool (3 g) are used. The resulting mixture is a clear, homogeneous solution of linalool (~2.7%) in aqueous Na-MOG. In a control experiment, linalool and water fail to produce a homogeneous mixture.

Example 15

Aqueous Vitamin E (α-Tocopherol) Composition

The procedure of Example 1 is followed except that MOG (22.6 g) and α-tocopherol (3 g) are used. The resulting mixture is a clear, homogeneous solution of α-tocopherol (~2.6%) in aqueous Na-MOG.

Example 16

Aqueous p-Cymene Composition

The procedure of Example 1 is followed except that monomenthyl succinate (MMS, 23.7 g) and p-cymene (3 g) are used. The resulting mixture is a clear, homogeneous solution of p-cymene (~2.5%) in aqueous sodium monomenthyl succinate (Na-MMS).

The examples are meant only as illustrations. The following claims define the invention.

We claim:

1. A clear aqueous composition which comprises:
   (a) from 55 to 98 wt. % of water;
   (b) from 0.1 to 10 wt. % of a hydrophobic organic compound; and
   (c) from 2 to 50 wt. % of an alkali metal or alkaline earth metal salt of a monoester of l-menthol and a saturated dicarboxylic acid.

2. The composition of claim 1 wherein the monoester salt is produced from a cyclic anhydride selected from the group consisting of glutaric anhydride, succinic anhydride, and adipic anhydride.

3. The composition of claim 1 wherein the monoester salt is selected from the group consisting of alkali metal salts of monomenthyl glutarate, monomenthyl 3-methylglutarate, monomenthyl 2-methylglutarate, monomenthyl succinate, monomenthyl 2-methylsuccinate, monomenthyl adipate, and mixtures thereof.

4. The composition of claim 1 wherein the hydrophobic organic compound is a physiological cooling agent, a physiological warming agent, a vitamin, a pharmaceutical or medicinal agent, a dietary supplement, a cosmetic ingredient, a flavoring agent, a fragrance ingredient, or a mixture thereof.

5. The composition of claim 1 wherein the hydrophobic organic compound is one or more biologically active compounds.

6. A consumer product that is prepared from or which comprises the composition of claim 1.

7. A process which comprises combining aqueous base with a mixture comprising the acid form of the monoester salt and the hydrophobic organic compound to produce the composition of claim 1.

8. A process which comprises combining the hydrophobic organic compound with an aqueous solution of the monoester salt to produce the composition of claim 1.

9. A clear aqueous composition which comprises:
   (a) from 55 to 98 wt. % of water;
   (b) from 0.1 to 10 wt. % of a physiological cooling agent; and
   (c) from 2 to 50 wt. % of an alkali metal monomenthyl glutarate.

* * * * *